(12) United States Patent
Ryu et al.

(10) Patent No.: US 9,296,888 B2
(45) Date of Patent: *Mar. 29, 2016

(54) RESIN BLEND

(71) Applicant: LG CHEM, LTD., Seoul (KR)

(72) Inventors: Jin Young Ryu, Daejeon (KR); Houng Sik Yoo, Seoul (KR); Hak Shin Kim, Daejeon (KR); Young Jun Hong, Daejeon (KR); Chong Kyu Shin, Daejeon (KR); Eun Joo Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/688,166

(22) Filed: Nov. 28, 2012

(65) Prior Publication Data

US 2013/0164485 A1 Jun. 27, 2013

Related U.S. Application Data

(63) Continuation-in-part of application No. PCT/KR2011/003884, filed on May 26, 2011.

(30) Foreign Application Priority Data

| May 28, 2010 | (KR) | 10-2010-0050639 |
| Aug. 20, 2010 | (KR) | 10-2010-0081084 |
| Apr. 11, 2011 | (KR) | 10-2011-0033147 |

(51) Int. Cl.
*C08L 29/04* (2006.01)
*B32B 3/02* (2006.01)
(Continued)

(52) U.S. Cl.
CPC ............. *C08L 33/12* (2013.01); *B29C 47/0004* (2013.01); *B29C 47/065* (2013.01); *B32B 3/02* (2013.01); *B32B 27/08* (2013.01); *C08J 3/005* (2013.01); *C08J 5/00* (2013.01); *C08L 9/00* (2013.01); *C08L 25/12* (2013.01); *C08L 29/04* (2013.01); *C08L 33/04* (2013.01); *C08L 33/16* (2013.01);
(Continued)

(58) Field of Classification Search
None
See application file for complete search history.

(56) References Cited

U.S. PATENT DOCUMENTS

| 4,159,288 A | 6/1979 | Carson et al. |
| 5,283,302 A * | 2/1994 | Wakamori et al. ............ 526/216 |

(Continued)

FOREIGN PATENT DOCUMENTS

| CN | 1132660 A | 10/1996 |
| CN | 101299074 A | 11/2008 |

(Continued)

OTHER PUBLICATIONS

English Abstract of Janado et al. JP 2006-143882, Jun. 2006.*
(Continued)

*Primary Examiner* — Ronak Patel
(74) *Attorney, Agent, or Firm* — Rothwell, Figg, Ernst & Manbeck

(57) ABSTRACT

Provided are a resin blend for melt processing, a pellet and a method of preparing a resin article using the same. The resin blend may include a first resin, and a second resin having a difference in surface energy from the first resin at 25° C. of 0.1 to 35 mN/m. The resin blend can improve mechanical and surface characteristics of a resin article. Further, since coating or plating is not required for manufacturing a resin article, a manufacturing time and/or cost can be reduced, and productivity can be increased.

3 Claims, 3 Drawing Sheets

(51) Int. Cl.
| | |
|---|---|
| B32B 27/08 | (2006.01) |
| C08L 33/12 | (2006.01) |
| C08L 9/00 | (2006.01) |
| C08J 3/00 | (2006.01) |
| C08J 5/00 | (2006.01) |
| C08L 33/04 | (2006.01) |
| C08L 101/00 | (2006.01) |
| C08L 33/16 | (2006.01) |
| C08L 37/00 | (2006.01) |
| C08L 55/02 | (2006.01) |
| C08L 101/12 | (2006.01) |
| B29C 47/00 | (2006.01) |
| B29C 47/06 | (2006.01) |
| C08L 25/12 | (2006.01) |
| G01N 21/3563 | (2014.01) |
| B29K 29/00 | (2006.01) |
| B29K 33/00 | (2006.01) |
| B29K 105/00 | (2006.01) |

(52) U.S. Cl.
CPC ............... *C08L 37/00* (2013.01); *C08L 55/02* (2013.01); *C08L 101/00* (2013.01); *C08L 101/12* (2013.01); *B29K 2029/04* (2013.01); *B29K 2033/12* (2013.01); *B29K 2105/0088* (2013.01); *B29K 2105/0094* (2013.01); *C08J 2300/00* (2013.01); *C08J 2300/22* (2013.01); *C08J 2323/06* (2013.01); *C08J 2400/00* (2013.01); *C08J 2400/22* (2013.01); *C08L 2201/02* (2013.01); *G01N 21/3563* (2013.01); *Y10T 428/239* (2015.01); *Y10T 428/2998* (2015.01); *Y10T 428/31504* (2015.04)

(56) References Cited

U.S. PATENT DOCUMENTS

| | | | | |
|---|---|---|---|---|
| 5,354,595 | A | | 10/1994 | Yamamoto et al. |
| 5,589,028 | A | * | 12/1996 | Robinson et al. ......... 156/306.6 |
| 5,693,928 | A | * | 12/1997 | Egitto et al. ............. 204/157.15 |
| 5,733,657 | A | | 3/1998 | Macheras et al. |
| 5,859,176 | A | * | 1/1999 | Nakahashi et al. ........... 528/310 |
| 2003/0047229 | A1 | * | 3/2003 | Smith et al. .................. 138/137 |
| 2003/0198769 | A1 | | 10/2003 | Jing et al. |
| 2004/0049006 | A1 | * | 3/2004 | Aramaki et al. ............. 528/335 |
| 2004/0171773 | A1 | * | 9/2004 | Bu et al. ......................... 526/72 |
| 2006/0199871 | A1 | * | 9/2006 | Hale et al. ....................... 521/48 |
| 2010/0000601 | A1 | * | 1/2010 | Burchill ....................... 136/256 |

FOREIGN PATENT DOCUMENTS

| | | | |
|---|---|---|---|
| FR | 2374361 | A1 | 7/1978 |
| JP | 2000-239532 | A | 9/2000 |
| JP | 2004-148775 | A | 5/2004 |
| JP | 2004-204122 | A | 7/2004 |
| JP | 2006-89734 | A | 4/2006 |
| JP | 2006-265540 | A | 10/2006 |
| JP | 2007-332187 | A | 12/2007 |
| JP | 2008-239924 | A | 10/2008 |
| JP | 2008-248072 | A | 10/2008 |
| JP | 2008-303282 | A | 12/2008 |
| KR | 100203527 | B1 | 6/1999 |
| WO | 99/19387 | A1 | 4/1999 |
| WO | 99/19402 | A1 | 4/1999 |
| WO | WO 2009134653 | * | 11/2009 |

OTHER PUBLICATIONS

International Search Report issued in Int'l Appln. No. PCT/KR2011/003884 dated Feb. 24, 2012, 2 pages.
M. Wei et al.: "Core-Sheath Structure in Electrospun Nanofibers from Polymer Blends," Macromolecular Materials and Engineering, vol. 291, pp. 1307-1314, 2006.
B.J. Keestra et al.: "Two Component Injection Molding of Phase Separating Blends," International Polymer Processing, vol. 21, pp. 168-174, 2006.
N. Zhao et al.: "A Novel Ultra-hydrophobic Surface: Statically Non-wetting but Dynamically Non-sliding," Advanced Functional Materials, vol. 17, pp. 2739-2745, 2007.
M. Schnell et al.: "Evolution of viscosities and morphology for the two-phase system polyethylene oxide/poly (dimethylsiloxane)," Chemistry and Materials Science, Theologica Acta, vol. 47, pp. 469-476, 2008.
Supplementary European Search Report issued in European Patent Application No. 11 78 6928.9 on Dec. 5, 2013, 6 pages.
Supplementary European Search Report issued in European Patent Application No. 11 78 6929.7 on Dec. 5, 2013, 6 pages.
Supplementary European Search Report issued in European Patent Application No. 11 78 6930.5 on Oct. 30, 2013, 7 pages.
Office Action issued in European Patent Application No. 11 786 928.9-1303 on Aug. 1, 2014, 4 pages.
Office Action issued in Chinese Patent Application No. 2011800265365 on May 5, 2014 along with English translation, 19 pages.
Office Action issued in Chinese Patent Application No. 201180026536.5 on Feb. 17, 2015 along with English translation, 19 pages.
M. Wei et al.: "Core-Sheath Structure in Electrospun Nanofibers from Polymer Blends," Macromolecular Materials and Engineering, vol. 291, 2006, pp. 1307-1314.

* cited by examiner

RESIN BLEND

CROSS-REFERENCE TO RELATED APPLICATION

This application is a continuation-in-part of International Application PCT/KR2011/003884, with an international filing date of May 26, 2011, which claims priority to and the benefit of Korean Patent Application No. 2010-0050639, filed May 28, 2010, Korean Patent Application No. 2010-0081084, filed Aug. 20, 2010, and Korean Patent Application No. 2011-0033147, filed Apr. 11, 2011, the disclosures of which are incorporated herein by reference in their entireties.

BACKGROUND

Plastic resins have various applications including automobile parts, helmets, parts of electric devices, parts of textile spinning machines, toys or pipes because of their easy processability and excellent properties such as tensile strength, modulus of elasticity, heat resistance and impact resistance. Particularly, home appliance functions as home interior accessories as well as its own function as home appliance and parts of automobiles and toys are in direct contact with a human body, these products are required to be environment-friendly and to have excellent scratch resistance. However, plastic resins are generally decomposed by oxygen in the air, ozone and light and easily changed in color when exposed to an external environment for over a certain period of time. As a result, plastic resins suffer from decrease of weather resistance and strength, which makes them to be easily broken. Thus, an additional coating or plating process has been usually applied to plastic resins to improve these problems and surface properties. However, such a coating or plating process can drop efficiency and economic feasibility of a manufacturing process of plastic resins or generate large amount of toxic materials during the process or disposal of a product.

Accordingly, various methods have been suggested to improve properties of plastic resins such as scratch resistance, heat resistance and weather resistance without using an additional coating or plating process. For example, a method of adding inorganic particles to high molecule resins has been suggested to improve physical properties such as abrasion resistance and stiffness of the resins. However, this method may deteriorate the processability of plastic resins and impact strength and gloss due to the addition of inorganic particles.

SUMMARY OF THE INVENTION

The present invention provides a resin blend for melt processing. The resin blend can improve mechanical and surface characteristics of the resin article by enabling formation of a surface layer on the resin article through a layer separation. Further, since a step for separate coating or plating is not required for manufacturing the resin article, a manufacturing time and/or manufacturing cost can be reduced, and productivity can be increased.

The present invention further provides a pellet produced by using the resin blend and a method for preparing the pellet.

The present invention still further provides a method of preparing a resin article by using the resin blend or the pellet.

In one embodiment, a resin blend includes a first resin and a second resin having a difference in surface energy from the first resin at 25° C. of 0.1 to 35 mN/m.

In another embodiment, a pellet includes a core including a first resin and a shell including a second resin having a difference in surface energy from the first resin at 25° C. of 0.1 to 35 mN/m.

In another embodiment, a method of preparing a resin article includes melting a blend of a first and second resin to form a melt blend and processing the melt blend to form the resin article. A surface energy difference between the first resin and the second resin is 0.1 to 35 mN/m at 25° C.

In another embodiment, a method of preparing a resin article includes melting a pellet including a core including a first resin and a shell including a second resin to form a melt, and processing the melt to form the resin article. A surface energy difference between the first and second resins is 0.1 to 35 mN/m at 25° C.

In another embodiment, a resin blend for forming a layer-separated structure includes a first resin and a second resin having a lower surface energy than the first resin. The second resin is disposed between the first resin and an ambient air in response to a melting process.

In another embodiment, a resin blend for forming a layer-separated structure includes a base resin and a functional resin. A value of a surface energy of the functional resin is different from that of the base resin, and the value of the surface energy of the functional resin is dependent on the properties of the base resin.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EMBODIMENTS

Figure 1:
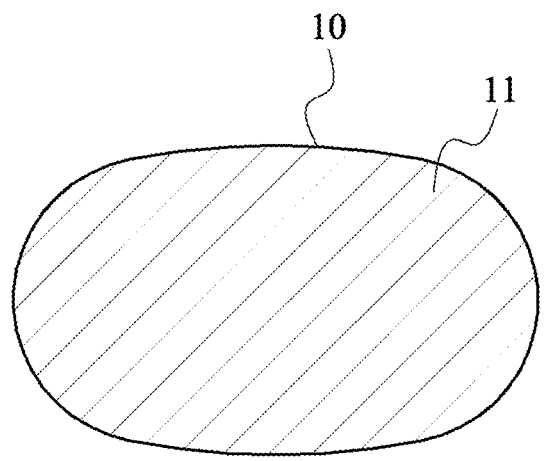
FIG. 1 is an illustrative schematic diagram showing a resin blend, according to one embodiment of the present invention.
Figure 2:
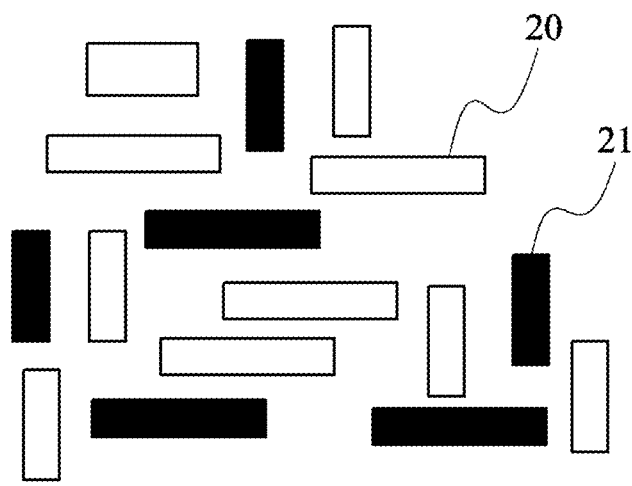
FIG. 2 is an illustrative schematic diagram showing a resin blend, according to another embodiment of the present invention.

Hereinafter, a resin blend for preparing a resin article having a surface layer formed as a result of a layer separation without a separate coating or plating process, a pellet and a method of preparing a resin article using the same according to embodiments of the present invention will be described in detail.

A "blend" may be a mixture of two or more different species of resins. A type of blend may include, but is not limited, a mixture of two or more resins in one matrix, or a mixture of two or more kinds of pellets. Particularly, the mixture of two or more resins in one matrix may be a pellet containing a mixture of two or more resins. For example, a mixture of a first resin and a second resin can be contained in a single pellet. Alternatively, in the mixture of two or more kinds of pellets each kind of pellet contains one kind of resin. For example, a blend can include a mixture of a pellet containing a first resin and a pellet containing a second resin A "melting process" or "melt processing" may refer to a process of melting the resin blend at not less than a melting temperature (Tm) of the resin blend to form a melt blend and forming a desired product by using the melt blend. For example, the melting process or melt process may include injection molding, extrusion, blow molding, expanding molding and the like.

A "layer separation" may indicate that a portion of a resin blend that is separated from the remaining resin blend by phase-separation, forms a layer that is visibly separated from a layer of the remaining resin blend. For example, the separated portion of the resin blend can be rich with or contain a substantial amount of a second resin and the remaining resin blend can be rich with or contain a substantial amount of a first resin. The layer separation results in a layer-separated structure in a resin article or a pellet, which is distinguished from a sea-island structure where the phase-separated portion is partially distributed in the entire resin blend. The layer separation of the resin blend results in two or more separate layers, preferably two separate layers formed in a resin article or a pellet prepared by the resin blend.

The present inventors confirmed through experimentation that a layer separation occurs when a resin blend comprising a first resin and a second resin having certain physical properties different from the first resin is used, and that such a layer separation enables to obtain substantially the same effects as applying a coating on a surface of pellets or resin articles without using additional process during or after melting process or melt processing such as extrusion or injection. Such a layer separation occurs during the melting process or melt processing and the second resin forms a surface layer on the pellets or the resin articles.

Thus, the resin blend for a melting process or melt processing according to one embodiment of the present invention may provide a resin article having improved mechanical and surface characteristics without the need of an additional processing such as coating or plating. In the past, a solvent with lower viscosity was used to remove a resin article easily from a mold. When the resin blend is used, a molecular weight distribution of a second resin and a difference in physical properties between a first resin and the second resin may cause the layer separation, which improves surface and mechanical properties of a resin article. For example, the resin blend of the present invention may be layer-separated by a melting process to form a resin article having a specific function on a surface of the resin article, without an additional process, such as coating and plating.

As such, the layer separation may be attributed to a difference in physical properties between first and second resins and/or a molecular weight distribution of the second resin. Here, the different physical properties may, for example, include surface energy, melt viscosity, glass transition temperature and a solubility parameter and the like. Although it is illustrated here that two resins are blended for the purpose of explanation of the present invention, it will be apparent to one of skilled in the art that three or more resins having different physical properties may be blended and separated during a melting process.

In one embodiment, a resin blend for melt processing comprises a first resin and a second resin having a difference in surface energy from the first resin at 25° C. of 0.1 to 35 mN/m.

The difference in surface energy between the first and second resins at 25° C. may be 0.1 to 35 mN/m, 1 to 30 mN/m, or 1 to 20 mN/m. The difference in surface energy between the first and second resins at 25° C. can also be 1 to 10 mN/m, 0.5 to 10 mN/m, 5 to 35, 15 to 35 mN/m or 5 to 30 mN/m. It will be apparent to one of skilled in the art that the listed ranges are only examples for the purpose of the description of the present invention and any values within 0.1 to 35 mN/m can be chosen. By way of an example, in the case that the resin blend of the first and second resins is melt-processed such as extrusion or injection, the melt-processed resin blend is exposed to an ambient air. In the melt-processed resin blend, the first and second resins can be separated due to the higher affinity of the second resin to the ambient air compared to the first resin. Particularly, the second resin having a smaller surface energy compared to the first resin may have a hydrophobic property, and due to its fluidity in the melt-processed resin blend, move to surface that contacts the ambient air. Thus, the second resin may be positioned adjacent to an ambient air to form a second resin layer as a surface layer. A first resin layer may be positioned on an inner side of the second layer. Accordingly, a layer separation can occur between the first and second resins of the resin blend. When the difference in surface energy is too low such as less than 0.1 mN/m, the layer separation of the melt-processed resin blend does not easily occur and the second resin in a mixture of melting state can be difficult to be positioned on the surface by moving through the matrix of the resin blend. When the difference in surface energy is too high such as greater than 35 mN/m, the first and second resins may not be attached to each other due to a high difference of surface energy, and thus may be detached.

The lower and/or upper limits of the difference in surface energy may be any numeric value of 0.1 to 35 mN/m, and be dependent on the properties of the first resin. Particularly, when a first resin is used as a base resin and a second resin is used a functional resin to improve surface properties of a first resin, the second resin may be selected such that a difference in surface energy between the first and second resins is 0.1 to 35 mN/m at 25° C. Since a value of the surface energy of the second resin (e.g., functional resin) may be different based on the properties of the first resin (e.g., base resin), the difference in surface energy may be determined based on the properties of the first resin. The properties of the first resin may include, but is not limited to, a kind of the first resin, or a value of the surface energy of the first resin. In one embodiment, the difference in surface energy may be selected by considering hydrophobicity of the second resin in a melting mixture of the first and second resins.

Figure 3:
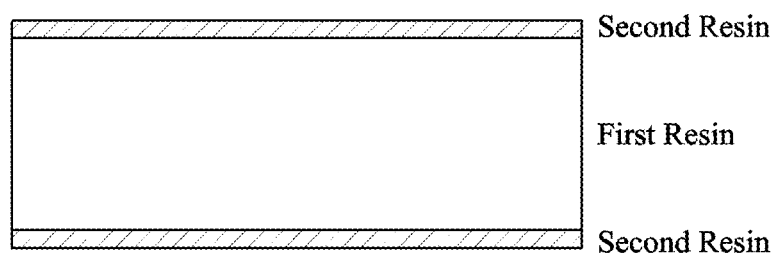
FIG. 3 is an illustrative schematic diagram showing a resin article formed by using a resin blend including a first resin and a second resin, according to one embodiment of the present invention.
Figure 4:
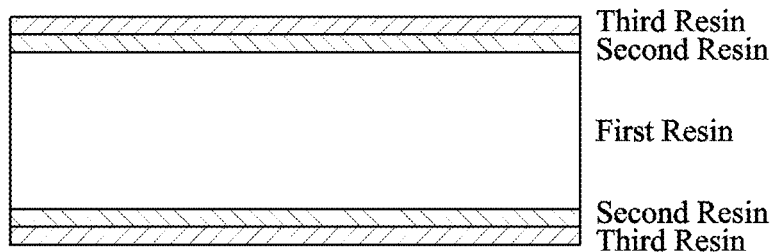
FIG. 4 is an illustrative schematic diagram showing a resin article formed by using a resin blend including a first resin, a second resin and a third resin, according to another embodiment of the present invention.
Figure 5:
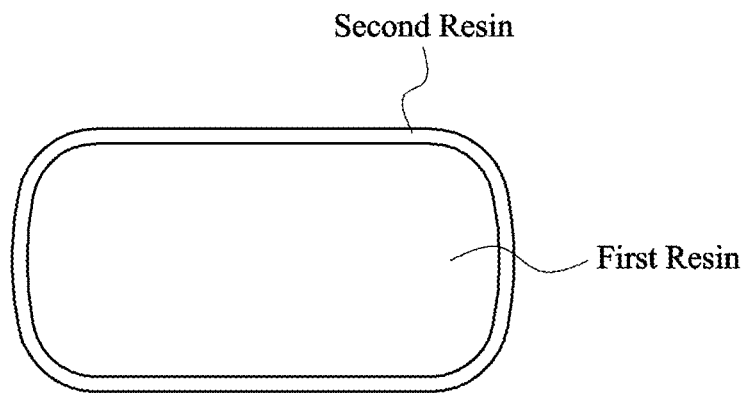
FIG. 5 is an illustrative schematic diagram showing a resin article, according to another embodiment of the present invention.

The resin blend may be separated into two or more layers. The resin blend including the first resin and the second resin may be layer-separated into three layers, i.e., Second resin layer/First resin layer/Second resin layer, as shown in FIG. 3, when two opposite sides of the melt-processed resin blend are exposed to the ambient air. Alternatively, when only one side of the melt-processed resin blend is exposed to the ambient air, the resin blend may be layer-separated into two layers, i.e., Second resin layer/First resin layer. Further, when a resin blend including a first resin, a second resin and a third resin is melt-processed, the melt-processed resin blend may be layer-separated into five layers, i.e., Third resin layer/Second resin layer/First resin layer/Second resin layer/Third resin layer, as shown in FIG. 4, by using the differences in surface energy among the three resins. Furthermore, when all sides of the melt-processed resin blend are exposed to the ambient air, the resin blend may be layer-separated into all direction to form a core-shell structure, as shown FIG. 5.

In another embodiment, a resin blend for a melt processing includes a first resin and a second resin having a difference in melt viscosity from the first resin of 0.1 to 3000 pa*s at a shear rate of 100 to 1000 s$^{-1}$ and at a processing temperature of the resin blend.

The difference in a melt viscosity between the first resin and the second resin may be 0.1 to 3000 pa*s, 1 to 2000 pa*s, or 1 to 1000 pa*s at a shear rate of 100 to 1000 s$^{-1}$ and at a processing temperature of the resin blend. The difference in a melt viscosity between the first resin and the second resin can also be 100 to 500 pa*s, 500 to 3000 pa*s, 1500 to 3000 pa*s, or 500 to 2500 pa*s at a shear rate of 100 to 1000 s$^{-1}$ and at a processing temperature of the resin blend. It will be apparent to one of skilled in the art that the listed ranges are only examples for the purpose of description of the present invention and any value within the range of 0.1 to 3000 pa*s at the above shear rate and at a processing temperature of the resin blend can be selected. When the difference in the melt viscosity is too low for example less than 0.1 pa*s at the shear rate and at a processing temperature of the resin blend, the layer separation of the melt-processed resin blend does not easily occur because the first and second resins are too easily mixed together. When the difference in the melt viscosity is too high for example greater than 3000 pa*s at the shear rate and at a processing temperature of the resin blend, the first and second resins may not be attached to each other due to a high difference of the melt viscosity and thus may be detached.

The lower and/or upper limits of the difference in melt viscosity may be any numeric value of 0.1 to 3000 pa*s, and be dependent on the properties of the first resin. Particularly, when a first resin is used as a base resin and a second resin is used as functional resin to improve surface properties of the first resin, the second resin may be chosen such that a difference in a melt viscosity between the first and second resins is 0.1 to 3000 pa*s at a shear rate of 100 to 1000 s$^{-1}$ and at a processing temperature of the resin blend. Since a value of the melt viscosity of the second resin (e.g., functional resin) may be different based on the properties of the first resin (e.g., base resin), the difference in the melt viscosity may be determined based on the properties of the first resin. The properties of the first resin may include, but is not limited to, a kind of the first resin, or a value of the melt viscosity of the first resin. In one embodiment, the difference in melt viscosity may be selected by considering fluidity of the second resin in a melt-processed blend of the first and second resins.

By way of an example, in the case that the resin blend of the first and second resins having the difference in melt viscosity of 0.1 to 3000 pa*s at a shear rate of 100 to 1000 s$^{-1}$ and at a processing temperature of the resin blend is used, when the resin blend of the first and second resins is melt-processed, the melt-processed resin blend is exposed to an ambient air. In the melt-processed resin blend, the first and second resins can be separated due to the difference of fluidity between the first resin and second resin. Particularly, the second resin having a smaller melt viscosity compared to the first resin may have a higher fluidity than the first resin, and move to a surface that contacts the ambient air. Thus, the second resin may be positioned adjacent to an ambient air to form a second resin layer as a surface layer. A first resin layer may be positioned on an inner side of the second layer. Accordingly, a layer separation can occur between the first and second resins of the resin blend.

The melt viscosity may be measured using a capillary flow meter, and indicates a shear viscosity (pa*s) at a predetermined processing temperature and shear rate (/s). The shear rate is a shear rate applied when the resin blend is processed, and may be selected depending on a processing method, for example, shear rate of 100 to 1000 s$^{-1}$. It will be apparent to one of skilled in the art to control the shear rate according to the processing method.

The processing temperature is a temperature at which the resin blend is processed. For example, when the resin blend is subject to a melt processing such as extrusion or injection, the processing temperature is a temperature at which the melt processing such as extrusion or injection is performed. The processing temperature may be controlled according to a resin subjected to melting processes such as extrusion or injection. It will be apparent to one of skilled in the art to control the processing temperature according to the kinds of resins of the resin blend. For example, a temperature for extruding or injecting a resin blend including a first a an ABS resin as a first resin and a second resin obtained by polymerizing a methyl methacrylate-based monomer may be 210 to 240° C.

In still another embodiment, a resin blend for a melt processing includes a first resin and a second resin having a difference in solubility parameter from the first resin at 25° C. of 0.001 to 10 $(J/cm^3)^{1/2}$.

The difference in a solubility parameter between the first resin and the second resin at 25° C. may be 0.001 to 10 $(J/cm^3)^{1/2}$, 0.01 to 5 $(J/cm^3)^{1/2}$, or 0.01 to 3 $(J/cm^3)^{1/2}$. The difference in a solubility parameter between the first resin and the second resin at 25° C. can also be 0.01 to 2 $(J/cm^3)^{1/2}$, 0.1 to 1 $(J/cm^3)^{1/2}$, 0.1 to 10 $(J/cm^3)^{1/2}$, 3 to 10 $(J/cm^3)^{1/2}$, 5 to 10 $(J/cm^3)^{1/2}$, or 3 to 8 $(J/cm^3)^{1/2}$. The lower and/or upper limit of the difference in solubility parameter may be any numeric value of 0.001 to 10 $(J/cm^3)^{1/2}$, and be dependent on a solubility parameter of the first resin. It will be apparent to one of skilled in the art that the listed values are only examples for the purpose of description of the present invention and any value within the range of 0.001 to 10 $(J/cm^3)^{1/2}$ at 25° C. can be chosen. A solubility parameter is an intrinsic property of resin reflecting solubility depending on a polarity of each resin molecule, and the solubility parameter for each resin is generally known. When the difference in the solubility parameter is too small, for example, less than 0.001 $(J/cm^3)^{1/2}$, the layer separation does not easily occur because the first and second resins are too easily mixed together. When the difference in the solubility parameter is too big, for example, greater than 10 $(J/cm^3)^{1/2}$, the first and second resins may not be attached to each other due to a high difference of solubility parameter, and thus may be detached.

The lower and/or upper limits of the difference in solubility parameter may be any numeric value of 0.001 to 10 $(J/cm^3)^{1/2}$, and be dependent on the properties of the first resin. Particularly, when a first and second resins are used as a base and functional resins, respectively, the second resin may be chosen such that a difference in a solubility parameter between the first and second resins is 0.001 to 10 $(J/cm^3)^{1/2}$ at 25° C. Since a value of the solubility parameter of the second resin (e.g., functional resin) may be different based on properties of the first resin (e.g., base resin), the difference in the solubility parameter may be determined based on the properties of the first resin. The properties of the first resin may include, but is not limited to, a kind of the first resin, or a value of the solubility parameter of the first resin. In one embodiment, the difference in solubility parameter may be selected by considering immiscibility between the first resin and the second resin in a melting mixture of the first and second resins.

By way of an example, in the case that the resin blend of the first and second resins having the difference in solubility parameter of 0.001 to 10 $(J/cm^3)^{1/2}$ at 25° C. is used, when the resin blend of the first and second resins is melt-processed, the melt-processed resin blend is exposed to an ambient air, the first and second resins can be separated due to the degree of immiscibility between the first resin and second resin. Particularly, the second resin having a difference in solubility parameter from the first resin at 25° C. of 0.001 to 10 $(J/cm^3)^{1/2}$ may be immiscible with the first resin. Thus, the second resin having additionally lower surface tension or lower melt viscosity than that of the first resin may move and be positioned adjacent to an ambient air to form a second resin layer. A first resin layer may be positioned on an inner side of the second layer. Accordingly, a layer separation can be occurred between the first and second resins of the resin blend.

In still another embodiment, a molecular weight distribution (PDI) of the second resin is 1 to 2.5 or 1 to 2.3. The molecular weight distribution can also be 1 to 2, 1.3 to 2.5, 1.5 to 2.5, or 1.3 to 2.3. The lower and/or upper limits of the molecular weight distribution (PDI) of the second resin may be any numeric value of 1 to 2.5. It will be apparent to one of skilled in the art that the listed ranges are only examples for the purpose of the description of the present invention and any value within the range of 1 to 2.5 can be selected. When the molecular weight distribution of the second resin is greater than 2.5, the first resin is easily mixed with the second resin due to the low molecular weight portion of the second resin, or the mobility of the second resin in a mixture of melting state is degraded due to the high molecular weight portion thereof, and thus the layer separation between the first resin and the second resin does not easily occur.

In still another embodiment, a weight average molecular weight (Mw) of the second resin of the resin blend is 30,000 to 200,000, or 50,000 to 150,000. The weight average molecular weight (Mw) of the second resin of the resin blend can also be 50,000 to 200,000, 80,000 to 200,000, 80,000 to 150,000, 50,000 to 120,000, or 80,000 to 120,000. The lower and/or upper limits of the weight average molecular weight (Mw) of the second resin may be any numeric value of 30,000 to 200,000. It will be apparent to one of skilled in the art that the listed ranges are only examples for the purpose of the description of the invention and any value within the range of 30,000 to 200,000 can be chosen. When the weight average molecular weight is smaller than 30,000, the first resin is easily mixed with the second resin, and when the weight average molecular weight is greater than 200,000, the mobility of the second resin in a mixture of melting state is degraded and thus the layer separation between the first and second resin does not easily occur.

Meanwhile, the first resin may determine the physical properties of a resin article and may be selected according to a kind of the desired resin article and processing conditions. As the first resin, any synthetic resin may be used without limitation, but may preferably include a styrene-based resin such as an acrylonitrile butadiene styrene (ABS)-based resin, a polystyrene-based resin, an acrylonitrile styrene acrylate (ASA)-based resin or a styrene-butadiene-styrene block copolymer-based resin; a polyolefin-based resin such as a high density polyethylene-based resin, a low density polyethylene-based resin or a polypropylene-based resin; a thermoplastic elastomer such as an ester-based thermoplastic elastomer or olefin-based thermoplastic elastomer; a polyoxyalkylene-based resin such as a polyoxymethylene-based resin or a polyoxyethylene-based resin; a polyester-based resin such as a polyethylene terephthalate-based resin or a polybutylene terephthalate-based resin; a polyvinylchloride-based resin; a polycarbonate-based resin; a polyphenylenesulfide-based resin; a vinyl alcohol-based resin; a polyamide-based resin; an acrylate-based resin; engineering plastics; or a copolymer or mixture thereof.

The engineering plastics are a group of plastics that exhibit superior mechanical and thermal properties. By way of examples, polyetherketone, polysulphone, polyimides and the like may be used as the engineering plastics.

The second resin shows the difference in physical properties from the first resin as described above, and may be chosen to provide specific functions to a surface of a resin article. The functions of the second resins are not particularly limited. For example, the second resins may be resins providing a high surface hardness function, an anti-wear function, an anti-contamination function, an anti-fingerprint function, a color, a pearling function, a high-gloss function, a non-gloss function, a barrier function or a combination thereof.

The second resin may have either or all of a thermal curable functional group and a radiation, such as UV, curable functional group without specific limitation. When a thermal curable functional group is included in the second resin, the layer separation occurs and hardness may be increased due to the crosslinks formed in melt processing such as extrusion or injection.

As another examples of the second resin, a (meth)acrylate-based resin, an epoxy-based resin, an oxetane-based resin, an isocyanate-based resin, a silicon-based resin, a fluorine-based resin, or a copolymer or mixture thereof may be included.

The (meth)acrylate-based resin is a resin formed by polymerizing an acryl or methacryl monomer as a main component, which may include, but is not limited to, alkyl methacrylates such as methyl methacrylate, ethyl methacrylate, propyl methacrylate, butyl methacrylate, cyclohexyl methacrylate, octyl methacrylate, lauryl methacrylate or stearyl methacrylate; alkyl acrylates such as methyl acrylate, ethyl acrylate, propyl acrylate, butyl acrylate, octyl acrylate, lauryl acrylate or stearyl acrylate; or glycidyl (meth)acrylates such as glycidyl methacrylate or glycidyl acrylate.

The epoxy-based resin is a resin containing an epoxy group, and may be, but is not limited to, a bisphenol type such as bisphenol A, bisphenol F, bisphenol S or a hydro additive thereof; a novolac type such as phenol novolac or cresol novolac; a nitrogen-containing ring type such as triglycidyl isocyanurate or hydantoin; an alicyclic type; an aliphatic type; an aromatic type such as naphthalene or biphenyl; a glycidyl type such as glycidyl ether, glycidyl amine or glycidyl ester; a dicyclo type such as dicyclopentadiene; an ester type; or an ether ester type.

The oxetane-based resin is a resin formed by polymerizing an oxetane monomer having at least one oxetane ring, and may be, but is not limited to, 1,4-bis[(3-ethyl-3-oxetanylmethoxy)methyl]benzene, di[1-ethyl(3-oxetanyl)]methylether, or a polyoxetane compound such as phenol novolac oxetane, terephthalate bisoxetane or biphenylene bisoxetane.

The isocyanate-based resin is a resin containing an isocyanate group, and may be, but is not limited to, diphenylmethane diisocyanate (MDI), toluene diisocyanate (TDI) or isophorone diisocyanate (IPDI).

The silicon-based resin is a resin containing a main chain connected by a siloxane bond which is a silicon-oxygen bond, and may be, but is not limited to, polydimethylsiloxane (PDMS).

The fluorine-based resin is a resin containing a fluorine atom, and may be, but is not limited to, polytetrafluoroethylene (PTFE), polychlorotrifluoroethylene (PCTFE), polyvinylidene fluoride (PVDF), or polyvinylfluoride (PVF).

The resin blend may include the second resin in an amount of 0.1 to 50 parts by weight, or 1 to 20 parts by weight, based on 100 parts by weight of the first resin. The amount of second resin may also be 0.1 to 35 parts by weight, 0.1 to 20 parts by weight, 5 to 50 parts by weight, 10 to 50 parts by weight, 5 to 35 parts by weight or 5 to 20 parts by weight, based on 100 parts by weight of the first resin. The lower and/or upper limits of the amount of the second resin included in the resin blend, may be any numeric value of 0.1 to 50 parts by weight based on 100 parts by weight of the first resin. It will be apparent to one of skilled in the art that the listed ranges are only examples for the purpose of the description of the present invention and any value within the range of 0.1 to 50 parts by weight can be chosen. When the second resin is included in an amount smaller than 0.1 parts by weight based on 100 parts by weight of the first resin, the layer separation does not occur. When the second resin is included in an amount greater than 50 parts by weight, the manufacturing cost increases due to the high cost of the second resin.

In another embodiment, a resin blend for forming a layer-separated structure includes a base resin and a functional resin. A value of a surface energy of the functional resin is different from that of the base resin, and the value of the surface energy of the functional resin is dependent on properties of the base resin.

The base resin, for example, a first resin, may substantially determine the physical properties of a resin article. The functional resin, for example, a second resin, may provide specific functions to a surface of a resin article. The properties of the base resin and the specific functions of the second resin are the same as described the above.

Figure 6:
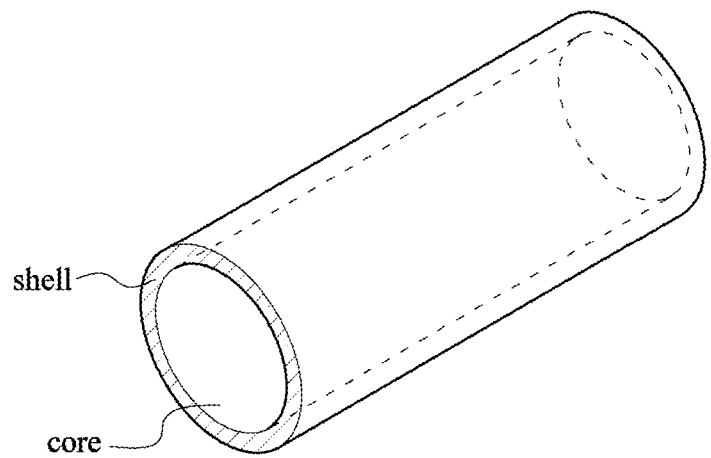
FIG. 6 is an illustrative schematic diagram showing a pellet having a core and a shell.

The present invention further provides a pellet prepared using the resin blend described above. The pellet may have a core having a first resin and a shell having a second resin formed on a surface of the pellet by layer separation. The first resin is disposed in the middle thereof (core), and a second resin is layer-separated from the first resin and disposed to surround the first resin and to form a shell of the pellet. The structure of a pellet can be illustrated as shown in FIG. 6.

The first resin and the second resin have different properties as described above. For example, the first resin and the second resin may have a difference in surface energy from the first resin at 25° C. of 0.1 to 35 mN/m; a difference in melt viscosity of 0.1 to 3000 pa*s at a shear rate of 100 to 1000 s$^{-1}$ and at a processing temperature of the pellet; or a difference in solubility parameter of 0.001 to 10.0 $(J/cm^3)^{1/2}$ at 25° C. Further, the second resin may have a molecular weight distribution (PDI) of 1 to 2.5 or a weight average molecular weight (Mw) of 30,000 to 200,000. The first and second resins have already been described in detail, and thus further detailed description will be omitted.

The present invention still further provides a method of preparing a resin article comprising a melt processing of the resin blend as described above. The resin article prepared has a layer-separated structure. In one embodiment, the method includes melting a blend of first and second resins to form a melt blend and processing the melt blend to prepare a resin article and the surface energy difference between the first resin and the second resin is 0.1 to 35 mN/m at 25° C.

As described above, since the second resin has a different physical property from the first resin such as higher hydrophobicity, the layer separation may occur during the melt processing such as injection or extrusion of the resin blend. This layer separation enables a layer of the second resin to be formed on a surface of pellets or a resin article without the need of additional process and thus provides the same results as applying a coating on a surface of pellets or a resin article by a separate step. Further, since the second resin can be formed to have a function such as gloss or anti-contamination and can be separated from the first resin during the melt processing of the resin blend, the resin article in which the first resin constitutes a body and the second resin forms a surface on the body can be easily manufactured without performing additional process. Still further, when the first and second resins are used to form a pellet, the pellet having a core of the first resin and a shell of the second resin can be manufactured by the melt processing of the resin blend without performing any additional process. Furthermore, The melt processing may be performed under a shear stress, and may include, but is not limited to, injection and extrusion.

In one embodiment, the resin blend may be prepared to include a first resin and a second resin that have a difference in physical properties, for example, surface energy, melt viscosity or solubility parameter. The resin blend may be melted to form a melt blend and the melt blend may be further processed to form pellets or a resin article. For example, the melted resin blend may be subject to an extrusion process to prepare a pellet. As described above, the first and second resins may be separated during the melt processing such as extrusion. Particularly, the second resin may move to contact with an ambient air due to its hydrophobic property compared to the first resin. A second resin layer may be positioned adjacent to an ambient air, and a layer substantially formed of a first resin layer may be positioned on an inner side of the second resin layer. Accordingly, the resin article may have a body that is formed of the first resin and a surface that is on the body and is formed of the second resin. Further, by the above described process, the pellet may have structure in which the first resin is disposed in the middle of the pellet and the second resin is disposed to surround the first resin.

In another embodiment, the pellet may be further processed, for example injection, to form a resin article. For example, the pellet having first and second resins of different physical properties may be melted and further processed, for example, injected, to form a final product, for example, a resin article. As described above, due to the difference in various physical properties, for example, surface energy, melt viscosity or solubility parameter, of the first and second resins of the pellets, the resin article formed of the pellets may have separated layers, i.e., a body formed of the first resin and a surface layer formed of the second resin and placed on the body. Although it is illustrated that the pellets of core-shell structure having the first and second resins are melt-processed to form a resin article for the purpose of explanation, it will be apparent to one of skilled in the art that a mixture of two or more pellets or pellets including the composition of two or more resins may be used to form a resin article. Alternatively, the resin blend may be directly prepared into a resin article through the melt processing such as injection, as described above. The processing temperature to be applied may be changed depend on kinds of the first and second resins used in the melt processing of the resin blend.

In some embodiments, the method of preparing a resin article may further include curing a product having a layer-separated structure (for example, a resin article having a body and a surface layer on the body) obtained from the melt processing of the resin blend. For example, after an extrusion or injection, thermal curing and/or radiation curing, such as UV curing, may be further performed on the melt-processed product. When necessary, chemical or physical treatment, such as a heat treatment, may be performed after the process.

Meanwhile, the method of preparing a resin article may further include preparing a second resin before the melt processing of the resin blend. The second resin may be selected depending on a first resin, as described above. For example, the second resin may be selected such that a value of a surface energy of the second resin is less than that of the first resin. Further, the second resin may be selected to add specific functions on a surface of the resin article. As examples for the preparation of the second resin, there is bulk polymerization, solution polymerization, suspension polymerization, or emulsion polymerization.

In the suspension polymerization method, the second resin may be prepared by dispersing a monomer in a reaction medium, adding and blending an additive such as a chain transfer agent, an initiator and a dispersion stabilizer in the reaction solvent and polymerizing the blend at 40° C. or higher. One of skilled in the art can easily select the kind of monomer based on a desired function such as an abrasion resistance function, an anti-wear function, an anti-contamination function, an anti-fingerprint function, a colored function, a pearl function, a high-gloss function, a non-gloss function and a barrier function. By way of examples of the monomer, there are (meth)acrylate monomers, epoxy monomers, oxetane monomers, isocyanate monomers, silicon monomers, fluorine-based monomers or a copolymer thereof.

The reaction medium may be any medium known to be conventionally used to prepare a synthetic resin, polymer or copolymer without limitation. For example, the reaction medium may be distilled water. The chain transfer agent which can be added to the reaction solvent may be, but is not limited to, an alkyl or aryl mercaptan such as n-butyl mercaptan, n-dodecyl mercaptan, tertiary dodecyl mercaptan, isopropyl mercaptan or aryl mercaptan; a halogen compound such as ketone tetrachloride; or an aromatic compound such as an alpha-methylstyrene dimer or an alpha-ethylstyrene dimer. The initiator is a polymerization initiator, which may be, but is not limited to, a peroxide such as octanoyl peroxide, decanoyl peroxide or lauroyl peroxide, or an azo-based compound such as azobisisobutyronitrile or azobis-(2,4-dimethyl)-valeronitrile. The dispersion stabilizer which can be included in the reaction medium may be, but is not limited to, an organic distribution agent such as polyvinyl alcohol, polyolefin-maleic acid or cellulose, or an inorganic distribution agent such as tricalcium phosphate.

The first and second resins have already been described above in detail, and thus further description thereof will be omitted. The present invention will be described with reference to the following Examples in detail. However, the present invention is not limited to the following Examples.

Measurement of Surface Energy

According to the Owens-Wendt-Rabel-Kaelble (OWRK) method, surface energies of first resins and second resins were measured using a drop shape analyzer (Kruss, DSA100). More specifically, the first resins and second resins were dissolved in a methyl ethyl ketone solvent to have a concentration of 15 wt %, and then coated on a LCD glass by bar coating. The coated LCD glass was pre-dried in an oven at 60° C. for 2 minutes and then dried at 90° C. for 1 minute. After drying (or curing), deionized water and diiodomethane were dropped 10 times on the coated surface at 25° C., respectively, to get an average value of a contact angle, and surface energy was calculated by substituting a numerical value into the OWRK method.

Measurement of Melt Viscosity

Melt viscosities of first resins and second resins were measured using a Capillary Rheometer 1501 (Gottfert). More specifically, after a capillary die was attached to a barrel, the first resins and second resins were put into the barrel by dividing to 3 parts. A shear viscosity (pa*s) according to a shear rate of 100 to 1000 s$^{-1}$ was measured at a processing temperature of 240° C.

Measurement of Solubility Parameter

While there are some methods of measuring and calculating solubility parameters, the solubility parameters of first resins and second resins were calculated at 25° C. using a known method, the Van Krevelen method [refer to Bicerano, J., Prediction of Polymer Properties, third edition, Marcel Dekker Inc., New York (2002), the disclosure of which is incorporated herein by reference in its entirety]. According to the Van Krevelen method, the solubility parameter was calculated using a group contribution theory, and defined as the following formula:

$$\delta \text{ (solubility parameter)} = \sqrt{e_{coh}} = \sqrt{\frac{E_{coh}}{V}}$$

In the formula, $E_{coh}$ is a cohesive energy, V is a molar volume, and $e_{coh}$ is a cohesive energy density. The cohesive energy ($E_{coh}$) is defined as follows:

$$E_{coh} = 10570.9 \times (^0X^v - ^0X) + 9072.8 \times (2 \times ^1X - ^1X^v) + 1018.2 \times N_{VKH}$$

In the formula, $^0X$, $^1X$, $^0X^v$ and $^1X^v$ are connectivity indices, and $N_{VKH}$ is a correlation term. Each variant was calculated with reference to the disclosed literature [Bicerano, J., Prediction of Polymer Properties, third edition, Marcel Dekker Inc., New York (2002)].

Observation of Feature of Cross-Section

Samples went through a low temperature impact test. Then, fracture surfaces of the samples were etched using THF vapor, and a layer-separated cross-section was observed using an SEM.

Experiment for Measuring Pencil Hardness

Pencil hardness of samples was measured under a constant load of 500 g using a pencil hardness tester (Chungbuk Tech). Scratches were made on a surface of the samples by standard pencils (Mitsubishi; grade 6B to 9H) with a fixed angle of 45 degrees, and therefore a change rate of the surface was observed (ASTM 3363). The values of pencil hardness are average values of the results obtained from tests performed 5 times.

Measurement of Molecular Weight Distribution (PDI)

Molecular weight distribution was measured using gel permeation chromatography (GPC) under conditions as follows:

Instrument: 1200 series produced by Agilent Technologies
Column: 2 PLgel mixed Bs produced by Polymer Laboratories
Solvent: THF
Column Temperature: 40° C.
Concentration of Sample: 1 mg/mL, 100 L injection
Standard: Polystyrene (Mp: 3900000, 723000, 316500, 52200, 31400, 7200, 3940 or 485)

As an analysis program, ChemStataion provided by Agilent Technologies was used, and a weight average molecular weight (Mw) and a number average molecular weight (Mn) were measured using gel permeation chromatography (GPC), and the molecular weight distribution was then calculated from an equation of Mw/Mn.

EXAMPLE 1

(1) Preparation of First Resin and Second Resin

As a first resin, a first resin-1 (a thermoplastic resin composed of 60 wt % methyl methacrylate, 7 wt % acrylonitrile, 10 wt % butadiene and 23 wt % styrene) was used. As a second resin, a second resin-1 was prepared as following: 1500 g of distilled water and 4 g of 2% polyvinylalcohol aqueous solution as a dispersing agent were put into a 3-liter reactor and dissolved. Subsequently, 560 g of methyl methacrylate, 240 g of glycidyl methacrylate, 2.4 g of n-dodecyl mercaptan as a chain transfer agent and 2.4 g of azobisisobutyronitrile as an initiator were further added thereto, and mixed while stirring at 400 rpm. The mixture was polymerized by 3-hour reaction at 60° C., and cooled to 30° C., thereby obtaining a bead-type second resin-1. Afterward, the second resin-1 was washed three times with distilled water, dehydrated and dried in an oven.

As the results of measurement of the physical properties of the first resin-1 and the second resin-1, it was shown that a difference in surface energy was 6.4 mN/m, a difference in melt viscosity was 180 pa*s, a difference in solubility parameter was 0.5 (J/cm3)1/2, a weight average molecular weight of the second resin obtained by GPC was 100K, and a molecular weight distribution (PDI) of the second resin was 2.1.

(2) Preparation of Resin Blend and Resin Article Using the Same

Figure 7:
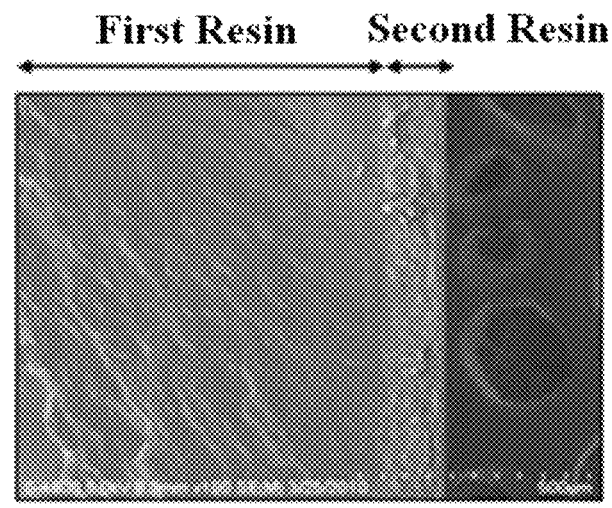
FIG. 7 is a SEM image illustrating a cross-sectional view of a resin article prepared according to Example 1.

After 90 parts by weight of the first resin-1 was blended with 10 parts by weight of the second resin-1, the blend was extruded using a twin-screw extruder (Leistritz) at 240° C., thereby obtaining a pellet. A layer separation was observed in the pellet. Then, the pellet was injected using an EC100Φ30 injector (ENGEL) at 240° C., thereby obtaining a sample 1 having a thickness of 3200 µm. A pencil hardness of the sample 1 was 2H, and layer separation occurred. The feature of the cross-section of the sample 1 observed by using SEM is shown in FIG. 7

EXAMPLE 2

(1) Preparation of First Resin and Second Resin

As a first resin, the first resin-1 of Example 1 was used. As a second resin, a second resin-2 was prepared as following: 1500 g of distilled water and 4 g of 2% polyvinylalcohol aqueous solution as a dispersing agent were put into a 3-liter reactor and dissolved. Subsequently, 760 g of methyl methacrylate, 40 g of perfluorohexylethyl methacrylate, 2.4 g of n-dodecyl mercaptan as a chain transfer agent and 2.4 g of azobisisobutyronitrile as an initiator were further added thereto, and mixed while stirring at 400 rpm. The mixture was polymerized by 3-hour reaction at 60° C., and cooled to 30° C., thereby obtaining a bead-type second resin-2. Afterward, the second resin-2 was washed three times with distilled water, dehydrated and dried in an oven.

As the results of measurement of the physical properties of the first resin-1 and the second resin-2, it was shown that a difference in surface energy was 4.2 mN/m, a difference in melt viscosity was 250 pa*s, a difference in solubility parameter was 0.2 (J/cm$^3$)$^{1/2}$, a weight average molecular weight of the second resin obtained by GPC was 100K, and a molecular weight distribution (PDI) of the second resin was 2.0.

(2) Preparation of Resin Blend and Resin Article Using the Same

A sample 2 having a thickness of 3200 µm was prepared by the same method as Example 1, except that 10 parts by weight of the second resin-2 was used instead of 10 parts by weight of the second resin-1. A pencil hardness of the sample 2 was 2H, and layer separation occurred.

EXAMPLE 3

(1) Preparation of First Resin and Second Resin

As a first resin, the first resin-1 of Example 1 was used. As a second resin, a second resin-3 was prepared by the same method as described in Example 1, except that 560 g of methyl methacrylate, 240 g of tertiary butyl methacrylate, 2.4 g of n-dodecyl mercaptan as a chain transfer agent and 3.2 g of azobisisobutyronitrile as an initiator were put into the reactor.

As the results of measurement of the physical properties of the first resin-1 and the second resin-3, it was shown that a difference in surface energy was 1.1 mN/m, a difference in melt viscosity was 360 pa*s, a difference in solubility parameter was 0.7 (J/cm$^3$)$^{1/2}$, a weight average molecular weight of the second resin obtained by GPC was 80K, and a molecular weight distribution (PDI) of the second resin was 1.9.

(2) Preparation of Resin Blend and Resin Article Using the Same

A sample 3 having a thickness of 3200 µm was prepared by the same method as Example 1, except that 10 parts by weight of the second resin-3 was used instead of 10 parts by weight of the second resin-1. A pencil hardness of the sample 3 was 2H, and layer separation occurred.

EXAMPLE 4

(1) Preparation of First Resin and Second Resin

As a first resin, a first resin-2 (a thermoplastic resin composed of 21 wt % of acrylonitrile, 15 wt % of butadiene and 64 wt % of styrene) was used. As a second resin, the second resin-1 of Example 1 was used.

As the results of measurement of the physical properties of the first resin-2 and the second resin-1, it was shown that a difference in surface energy was 6.1 mN/m, a difference in melt viscosity was 120 pa*s, a difference in solubility parameter was 0.7 (J/cm$^3$)$^{1/2}$, a weight average molecular weight of the second resin obtained by GPC was 100K, and a molecular weight distribution (PDI) of the second resin was 2.1.

(2) Preparation of Resin Blend and Resin Article Using the Same

A sample 4 having a thickness of 3200 µm was prepared by the same method as described in Example 1, except that 90 parts by weight of the first resin-2 was used instead of 90 parts by weight of the first resin-1. A pencil hardness of the sample 4 was HB, and layer separation occurred.

COMPARATIVE EXAMPLE 1

Comparative Example 1 was prepared with only the first resin-1 of Example. Particularly, 100 parts by weight of the first resin-1 of Example 1 was extruded using a twin-screw extruder (Leistritz) at 240° C., thereby obtaining a pellet. Then, the pellet was injected using an EC100Φ30 injector (ENGEL) at 240° C., thereby obtaining a sample 5 having a thickness of 3200 µm.

As the results obtained by measuring physical properties of the sample 5, a pencil hardness was F, and layer separation was not observed.

COMPARATIVE EXAMPLE 2

100 parts by weight of the first resin-2 of Example 4 was extruded using a twin-screw extruder (Leistritz) at 240° C., thereby obtaining a pellet. Then, the pellet was injected using an EC100Φ30 injector (ENGEL) at 240° C., thereby obtaining a sample 6 having a thickness of 3200 µm.

As the results obtained by measuring physical properties of the sample 6, a pencil hardness was 2B, and layer separation was not observed.

COMPARATIVE EXAMPLE 3

(1) Preparation of First Resin and Second Resin

As a first resin, the first resin-1 of Example 1 was used. As a second resin, a second resin-4 was prepared as following: 1500 g of distilled water and 4 g of 2% polyvinylalcohol aqueous solution as a dispersing agent were put into a 3-liter reactor and dissolved. Subsequently, 40 g of methyl methacrylate, 760 g of perfluorohexylethyl methacrylate, 2.4 g of n-dodecyl mercaptan as a chain transfer agent and 2.4 g of azobisisobutyronitrile as an initiator were further added thereto, and mixed while stirring at 400 rpm. The mixture was polymerized by 3-hour reaction at 60° C., and cooled to 30° C., thereby obtaining a bead-type second resin-4. Afterward, the second resin-4 was washed three times with distilled water, dehydrated and dried in an oven.

As the results of measurement of the physical properties of the first resin-1 and the second resin-4, it was shown that a difference in surface energy was 37 mN/m, a difference in melt viscosity was 375 pa*s, a difference in solubility parameter was 3.5 $(J/cm^3)^{1/2}$, a weight average molecular weight of the second resin measured by GPC was 100K, and a molecular weight distribution (PDI) of the second resin was 2.1.

(2) Preparation of Resin Blend and Resin Article Using the Same

A sample 7 having a thickness of 3200 μm was prepared by the same method as described in Example 1, except that 10 parts by weight of a second resin-4 was used instead of 10 parts by weight of the second resin-1. A detachment between the first resin and the second resin in the sample 7 occurred, and thus a pencil hardness was not measured.

COMPARATIVE EXAMPLE 4

(1) Preparation of First Resin and Second Resin

As a first resin, the first resin-1 of Example 1 was used. As a second resin, a second resin-5 was prepared by the same method as described in Example 1, except that 0.8 g of n-dodecyl mercaptan and 1.6 g of azobisisobutyronitrile were used instead of 2.4 g of n-dodecyl mercaptan and 2.4 g of azobisisobutyronitrile.

As the results of measurement of the physical properties of the first resin-1 and the second resin-5, it was shown that a difference in surface energy was 6.3 mN/m, a difference in melt viscosity was 1090 pa*s, a difference in solubility parameter was 0.5 $(J/cm^3)^{1/2}$, a weight average molecular weight of the second resin obtained by GPC was 205K, and a molecular weight distribution (PDI) of the second resin was 3.3.

(2) Preparation of Resin Blend and Resin Article Using the Same

A sample 8 having a thickness of 3200 μm was prepared by the same method as Example 1, except that 10 parts by weight of the second resin-5 was used instead of 10 parts by weight of the second resin-1. A pencil hardness of the sample 8 was H, layer separation was partially observed, and a thickness of separated layer was non-uniform in parts.

COMPARATIVE EXAMPLE 5

(1) Preparation of First Resin and Second Resin

As a first resin, the first resin-1 of Example 1 was used. As a second resin, a second resin-6 was prepared by the same method as described in Example 3, except that 4.8 g of n-dodecyl mercaptan and 2.4 g of azobisisobutyronitrile were used instead of 2.4 g of n-dodecyl mercaptan and 3.2 g of azobisisobutyronitrile.

As the results of measurement of the physical properties of the first resin-1 and the second resin-6, it was shown that a difference in surface energy was 1 mN/m, a difference in melt viscosity was 610 pa*s, a difference in solubility parameter was 0.7 $(J/cm^3)^{1/2}$, a weight average molecular weight of the second resin was 42K, and a molecular weight distribution (PDI) of the second resin was 3.2.

(2) Preparation of Resin Blend and Resin Article Using the Same

A sample 9 having a thickness of 3200 μm was prepared by the same method as described in Example 3, except that 10 parts by weight of a second resin-6 was used instead of 10 parts by weight of the second resin-3. A pencil hardness of the sample 9 was F, and layer separation was not observed.

COMPARATIVE EXAMPLE 6

(1) Preparation of First Resin and Second Resin

As a first resin, the first resin-1 of Example 1 was used. As a second resin, a second resin-7 was prepared by the same method as described in Example 3, except that 0.5 g of n-dodecyl mercaptan and 1.6 g of azobisisobutyronitrile were used instead of 2.4 g of n-dodecyl mercaptan and 3.2 g of azobisisobutyronitrile.

As the results of measurement of the physical properties of the first resin-1 and the second resin-7, it was shown that a difference in surface energy was 1 mN/m, a difference in melt viscosity was 1390 pa*s, a difference in solubility parameter was 0.7 $(J/cm^3)^{1/2}$, a weight average molecular weight of the second resin was 245K, and a molecular weight distribution (PDI) of the second resin was 5.3.

(2) Preparation of Resin Blend and Resin Article Using the Same

A sample 10 having a thickness of 3200 μm was prepared by the same method as described in Example 3, except that 10 parts by weight of the second resin-7 was used instead of 10 parts by weight of the second resin-3. A pencil hardness of the sample 10 was F, and layer separation was not observed.

COMPARATIVE EXAMPLE 7

(1) Preparation of First Resin and Second Resin

As a first resin, the first resin-1 of Example 1 was used. As a second resin, a second resin-8 was prepared by the same method as described in Example 3, except that 0.4 g of n-dodecyl mercaptan and 1.1 g of azobisisobutyronitrile were used instead of 2.4 g of n-dodecyl mercaptan and 3.2 g of azobisisobutyronitrile.

As the results of measurement of the physical properties of the first resin-1 and the second resin-8, it was shown that a difference in surface energy was 1 mN/m, a difference in melt viscosity was 2200 pa*s, a difference in solubility parameter was 0.7 $(J/cm^3)^{1/2}$, a weight average molecular weight of the second resin was 320K, and a molecular weight distribution (PDI) of the second resin was 5.2.

(2) Preparation of Resin Blend and Resin Article Using the Same

A sample 11 having a thickness of 3200 μm was prepared by the same method as described in Example 3, except that 10 parts by weight of the second resin-8 was used instead of 10 parts by weight of the second resin-3. A pencil hardness of the sample 11 was F, and layer separation was not observed.

As shown in Examples 1-4 and Comparative Examples 1-7, the layer separation was observed in Examples 1 to 4 using the first resin and second resin having the difference in surface energy, melt viscosity or solubility parameter as described herein. It was further observed that the resin article prepared according to the Examples 1 to 4 had a layer formed with the first resin and a layer formed with the second resin. Here, the first resin layer constituted the body of the resin article and the second resin layer constituted the surface on the body.

As the second resin layer was formed on a surface of the resin article by the melt processing, the resin article can have improved surface characteristics. More particularly, since the second resin polymerized from a methyl methacrylate-based monomer, as illustrated in Examples 1 to 5, could exhibit an excellent anti-scratch characteristic due to a high pencil hardness of HB or more, the resin article showed an improved hardness property. Although the hardness property was illustrated in the Examples 1-5 for the purpose of the description of the present invention, it will be obvious to one of skilled in the art that any other property can be added to the second resin to improve a property of a resin article.

On the other hand, the resin articles prepared using only the first resin (Comparative Examples 1 and 2) did not have separated layers and had low surface pencil hardness. Accordingly, to use the resin article obtained in Comparative Examples 1 and 2 for a part of an automobile or a part of an electric device, a coating process was needed to improve a surface characteristic.

Meanwhile, when the difference in surface energy between the first resin and the second resin was greater than 35 mN/m (Comparative Example 3), the first resin was not attached to the second resin and both resins were detached from each other. Therefore, it was understood that layer separation occurs only when the first resin and the second resin had a certain difference in surface energy (at 25° C.) like Examples 1 to 4.

In addition, it was understood from Comparative Examples 4 to 7 that the layer separation was observed only when the second resin had weight average molecular weight and molecular weight distribution as described the above.

While the invention has been shown and described with reference to certain exemplary embodiments thereof, it will be understood by those skilled in the art that various changes in form and details may be made therein without departing from the scope of the invention as defined by the appended claims.

What is claimed is:

1. A resin blend for melt processing, comprising:
    a first resin; and
    a second resin having a difference in surface energy from the first resin at 25° C. of 0.1 to 35 mN/m,
    wherein the resin blend contains a content of the second resin that is 0.1 to 50 parts by weight based on 100 parts by weight of the first resin,
    wherein the resin blend is capable of forming a layer-separated structure during melting process under a shear stress,
    wherein the second resin has a molecular weight distribution of 1.9 to 2.1 and a weight average molecular weight of 30,000 to 200,000, and
    wherein the second resin includes at least one selected from the group consisting of a (meth)acrylate-based resin, an epoxy-based resin, an oxetane-based resin, an isocyanate-based resin, and a copolymer thereof and wherein the first resin includes at least one selected from the group consisting of a styrene-based resin, a thermoplastic elastomer, a polyoxyalkylene-based resin, a polyvinyl chloride-based resin, a polycarbonate-based resin, a polyphenylene sulfide-based resin, a vinyl alcohol-based resin, an acrylate-based resin, engineering plastics and a copolymer thereof.

2. A resin blend for melt processing, comprising:
    a first resin; and a second resin having a difference in surface energy from the first resin at 25° C. of 0.1 to 35 mN/m, wherein the resin blend contains a content of the second resin that is 0.1 to 50 parts by weight based on 100 parts by weight of the first resin, wherein the resin blend is capable of forming a layer-separated structure during the melting process under a shear stress, wherein the second resin has a molecular weight distribution of 1.9 to 2.1 and a weight average molecular weight of 30,000 to 200,000, and wherein the second resin includes at least one selected from the group consisting of an anti-wear resin, an anti-contamination resin, an anti-fingerprint resin, a colored resin, a pearl resin, a high-gloss resin, a non-gloss resin and a barrier resin, and wherein the first resin includes at least one selected from the group consisting of a styrene-based resin, a thermoplastic elastomer, a polyoxyalkylene-based resin, a polyvinyl chloride-based resin, a polycarbonate-based resin, a polyphenylene sulfide-based resin, a vinyl alcohol-based resin, an acrylate-based resin, engineering plastics and a copolymer thereof.

3. A resin blend for forming a layer-separated structure,
    a base resin; and
    a functional resin having a difference in surface energy from the base resin at 25° C. of 0.1 to 35 mN/m,
    wherein the resin blend is capable of forming a layer-separated structure during the melting process under a shear stress,
    wherein the functional resin has a molecular weight distribution of 1.9 to 2.1 and a weight average molecular weight of 30,000 to 200,000,
    wherein the functional resin includes at least one selected from the group consisting of a (meth)acrylate-based resin, an epoxy-based resin, an oxetane-based resin, an isocyanate-based resin, and a copolymer thereof wherein the base resin includes at least one selected from the group consisting of a styrene-based resin, a thermoplastic elastomer, a polyoxyalkylene-based resin, a polyvinyl chloride-based resin, a polycarbonate-based resin, a polyphenylene sulfide-based resin, a vinyl alcohol-based resin, an acrylate-based resin, engineering plastics and a copolymer thereof,
    wherein a value of the surface energy of the functional resin is dependent on the properties of the base resin, and
    wherein the resin blend contains a content of the functional resin that is 0.1 to 50 parts by weight based on 100 parts by weight of the base resin.

* * * * *